(12) United States Patent
Hofel et al.

(10) Patent No.: US 10,457,617 B2
(45) Date of Patent: Oct. 29, 2019

(54) PROCESS AND PLANT FOR OBTAINING AN ETHYLENE PRODUCT IN A SUPERCRITICAL STATE

(71) Applicant: LINDE AKTIENGESELLSCHAFT, Munich (DE)

(72) Inventors: Torben Hofel, Munich (DE); Martin Kamann, Oberhaching (DE); Michael Scholch, Starnberg (DE); Sean McCracken, Puchheim (DE); Josef Kunkel, Gauting (DE); Gunther Kracker-Semler, Unterhaching (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 15/999,757

(22) PCT Filed: Feb. 20, 2017

(86) PCT No.: PCT/EP2017/053809
§ 371 (c)(1),
(2) Date: Aug. 20, 2018

(87) PCT Pub. No.: WO2017/140912
PCT Pub. Date: Aug. 24, 2017

(65) Prior Publication Data
US 2019/0144363 A1   May 16, 2019

(30) Foreign Application Priority Data

Feb. 19, 2016 (EP) .................................. 16156548

(51) Int. Cl.
*C07C 11/04* (2006.01)
*C07C 7/04* (2006.01)
*B01D 3/14* (2006.01)

(52) U.S. Cl.
CPC .............. *C07C 11/04* (2013.01); *B01D 3/143* (2013.01); *C07C 7/04* (2013.01); *B01D 2256/24* (2013.01);
(Continued)

(58) Field of Classification Search
None
See application file for complete search history.

(56) References Cited

U.S. PATENT DOCUMENTS 2,813,920 A    11/1957  Cobb, Jr.
3,969,196 A *  7/1976   Zosel ....................... B01D 3/00
                                                    203/49
(Continued)

FOREIGN PATENT DOCUMENTS

WO    2014/134703 A1    9/2014

OTHER PUBLICATIONS

Heinz Zimmermann et al.; "Ethylene" In: "Ullmann's Encyclopedia of Industrial Chemistry"; Apr. 15, 2009.

*Primary Examiner* — Tam M Nguyen
(74) *Attorney, Agent, or Firm* — Fay Sharpe LLP

(57) ABSTRACT

A method for obtaining an ethylene product in a supercritical state is proposed, in which method a gas mixture containing predominantly or exclusively ethylene and ethane is separated in a distillation column (1), which is operated at a distillation pressure level of from 5 to 15 bar, into an overhead product containing predominantly or exclusively ethylene and a bottom product containing predominantly or exclusively ethane, the overhead product being withdrawn in the gaseous state from the head of the distillation column (1) and a first portion thereof being liquefied and returned as reflux to the distillation column (1) and a second portion thereof being converted into a supercritical state and being used as the ethylene product. Provision is made that, for (Continued)

converting the second portion into the supercritical state, multi-stage compression from the distillation pressure level via a plurality of intermediate pressure levels to a supercritical pressure level is carried out, the second portion in the multi-stage compression being converted predominantly or exclusively from the gaseous into the supercritical state. A corresponding installation is likewise a subject of the invention.

12 Claims, 5 Drawing Sheets

(52) U.S. Cl.
CPC ..... *B01D 2257/7022* (2013.01); *Y02P 20/544* (2015.11); *Y02P 30/48* (2015.11)

(56) References Cited

U.S. PATENT DOCUMENTS

| | | | | |
|---|---|---|---|---|
| 4,568,447 | A * | 2/1986 | Pujado | C10G 45/02 208/177 |
| 5,520,724 | A * | 5/1996 | Bauer | C07C 7/11 95/169 |
| 7,687,048 | B1 * | 3/2010 | Schultz | B01D 53/1425 423/220 |
| 2019/0145703 | A1 * | 5/2019 | Hofel | F04D 17/12 |

* cited by examiner

PROCESS AND PLANT FOR OBTAINING AN ETHYLENE PRODUCT IN A SUPERCRITICAL STATE

The invention relates to a method for obtaining an ethylene product in a supercritical state and to a corresponding installation in accordance with the respective preambles of the independent claims.

PRIOR ART

Methods and corresponding installations for obtaining olefins such as ethylene by steam cracking are known and described for example in the article "Ethylene" in Ullmann's Encyclopedia of Industrial Chemistry, online since 15 Apr. 2009, DOI 10.1002/14356007.a10_045.pub3. In steam cracking, initially gas mixtures are obtained which can be subjected to processing and, for separating into components or groups of components, to separation sequences. For example, what are called "demethanizer first", "deethanizer first" and "depropanizer first" processes are known from the prior art.

The conventional target product of steam cracking, namely ethylene, is also separated off from the other components in corresponding separation sequences. To obtain ethylene, in a corresponding separation sequence a fraction which contains predominantly or exclusively ethane and ethylene is formed for this purpose. This fraction is separated in a distillation column, known as a C2 splitter, into a gaseous overhead product containing predominantly or exclusively ethylene and a liquid bottom product containing predominantly or exclusively ethane. The overhead product of the C2 splitter is returned in part in liquefied form to the C2 splitter as reflux, while a further portion can be provided as a liquid and/or gaseous ethylene product.

The present invention relates in particular to the use of what are known as low-pressure (LP) C2 splitters, which are operated at a pressure level of typically approximately 8 to 9 bar. The use of such low-pressure C2 splitters has advantages over the use of high-pressure (HP) C2 splitters in terms of capital costs and energy consumption. Low-pressure C2 splitters are described in the aforementioned article "Ethylene" in Ullmann's Encyclopedia of Industrial Chemistry in the section "Heat-Pumped C2 Fractionation" on page 47. Further details relating to the advantages of low-pressure C2 splitters are given therein.

Occasionally it has been required for the ethylene product to be provided in a supercritical state. To this end, in a method of the prior art which is not in accordance with the invention, which method is also discussed with reference to FIG. 1, the gaseous overhead product containing predominantly or exclusively ethylene from the head of the low-pressure C2 splitter can first of all be heated for example to ambient temperature, then compressed to a pressure level of for example more than 20 bar, and liquefied by cooling at this pressure level. Some of the liquefaction product obtained here is used as the aforementioned reflux to the C2 splitter. The remainder of the liquefaction product, or only a portion thereof, is conveyed by means of a pump from the liquid state to a supercritical pressure level and is heated to the supercritical pressure level.

As discussed in particular with reference to FIG. 5, a corresponding method is disadvantageous in terms of energy, since a large amount of energy is withdrawn during the cooling, and additional energy has to be supplied for the evaporation at the supercritical pressure level. There is therefore a requirement for improved processes and devices for providing gaseous ethylene at supercritical pressure from a gaseous overhead product containing predominantly or exclusively ethylene from the head of a low-pressure C2 splitter.

DISCLOSURE OF THE INVENTION

Against this background, the present invention proposes a method for obtaining an ethylene product in a supercritical state and a corresponding installation comprising the features of the independent claims. Embodiments are in each case the subject of the dependent claims and also of the following description.

Before discussing the features and advantages of the present invention, the basic principles thereof and the terms used will be discussed.

The present application uses the terms "pressure level" and "temperature level" to characterise pressures and temperatures, this being intended to express that pressures and temperatures in an appropriate installation do not have to be used in the form of exact pressure or temperature values in order to realise the inventive concept. However, such pressures and temperatures typically vary within certain ranges, which are for example ±1%, 5%, 10%, 20% or even 50% about a mean value. Corresponding pressure levels and temperature levels can in this case lie in disjoint ranges or in ranges which overlap one another. In particular, for example pressure levels also cover different pressures which result from unavoidable pressure drops. The equivalent applies to temperature levels. Pressure levels indicated here in bar are absolute pressures.

In methods and installations of the type discussed at the outset, multi-stage turbocompressors may be used for compression. The mechanical structure of turbocompressors is known in principle to a person skilled in the art. In a turbocompressor, the medium to be compressed is compressed by means of turbine blades which are arranged on a turbine impeller or directly on a shaft. A turbocompressor in this case forms a structural unit, which however in the case of a multi-stage compressor may have a plurality of compressor stages. In this case, as a rule, a compressor stage comprises a turbine impeller or a corresponding arrangement of turbine blades. All these compressor stages can be driven by a common shaft. However, provision may also be made for the compressor stages to be driven in groups using different shafts, it also being possible for the shafts to be interconnected via gear mechanisms.

A heat exchanger serves for indirect transfer of heat between at least two fluid streams which are guided for example in a reverse flow relative to each other. A heat exchanger for use in the context of the present invention may be formed from a single heat exchanger portion or a plurality of heat exchanger portions connected in parallel and/or in series, for example from one or more plate-type heat exchanger blocks.

With regard to the design and specific configuration of distillation columns as can be used in the context of the present application, reference is made to relevant textbooks (see for example K. Sattler, "Thermische Trennverfahren: Grundlagen, Auslegung, Apparate" ["Thermal separation processes: basic principles, design, apparatus"], 3rd edition, Wiley-VCH, Weinheim 2001).

A distillation column as stated here is a separating unit which is set up to separate, at least in part, a substance mixture (separation batch) which is provided in gaseous or liquid form or in the form of a two-phase mixture having liquid and gaseous portions, optionally also in the supercritical state, i.e. to produce from the substance mixture pure substances or substance mixtures in each case which, compared with the substance mixture, are enriched or depleted with respect to at least one component in the context discussed above. Distillation columns are well known from the field of separation technology. Typically, distillation columns are formed as cylindrical metal vessels which are equipped with built-in items, for example sieve trays or structured or random packing. A distillation column is distinguished inter alia in that a liquid fraction separates off in its lower region, also referred to as the bottom. This liquid fraction, also referred to as bottom product, is heated in a distillation column by means of a bottom evaporator, so that some of the bottom product continuously evaporates and ascends in gaseous form in the distillation column. A distillation column is further typically provided with an apparatus into which at least some of a gas mixture which becomes enriched in an upper region of the distillation column or a corresponding clean gas, also referred to as overhead product, is fed, is liquefied there and is charged as liquid reflux at the head of the distillation column.

Advantages of the Invention

The present invention proposes a method for obtaining an ethylene product in a supercritical state, in which a gas mixture containing predominantly or exclusively ethylene and ethane is separated in a distillation column, which is operated at a distillation pressure level of from 5 to 15 bar, in particular from 8 to 10 bar, for example approx. 8.1 bar, into an overhead product containing predominantly or exclusively ethylene and a bottom product containing predominantly or exclusively ethane. The distillation column used for separating the gas mixture is therefore a typical low-pressure C2 splitter. With regard to further features of such a low-pressure C2 splitter, reference is made to the above discussions and also to the relevant technical literature cited therein.

The overhead product formed in the distillation column is withdrawn in the gaseous state from the head of the distillation column and a first portion thereof is liquefied and returned as reflux to the distillation column. To form a second portion, the overhead product withdrawn in the gaseous state from the head of the distillation column is converted into a supercritical state and used as the ethylene product.

If what is being discussed here is that a first portion and a second portion of the overhead product are used in the manner discussed, this should be understood to mean that further portions of a corresponding overhead product can be used in other ways; for example, they may be provided as ethylene product in gaseous or liquid form in a subcritical state.

As already discussed, in methods of the prior art, as are also discussed with reference to FIG. 1, provision is made to heat a corresponding overhead product first of all for example to ambient temperature to provide an ethylene product in the supercritical state, then to compress it to a pressure level of for example more than 20 bar, and to liquefy it by cooling to this pressure level. In the prior art, the liquefaction product formed in this case is conveyed in a portion which corresponds to the second portion formed according to the invention from the liquid state to a supercritical pressure level and is heated at this supercritical pressure level.

By contrast, for converting the second portion into the supercritical state, the present invention proposes multi-stage compression from the distillation pressure level, i.e. the pressure level at which the distillation column is operated, and at which the overhead product is withdrawn from this distillation column, to compress via a plurality of intermediate pressure levels to a supercritical pressure level. The second portion is converted in this multi-stage compression predominantly or exclusively directly from the gaseous into the supercritical state. Therefore, in contrast with the prior art, no liquefaction and subsequent heating of a pressurised liquefaction product takes place. In other words, the conversion of the second portion into the supercritical state in the context of the present invention does not comprise any intermediate liquefaction. The present invention in this case has in particular energy-related advantages compared with the method of the prior art which has been discussed.

Since, according to the prior art, proceeding from the discussed pressure level at more than 20 bar and a correspondingly elevated temperature level (for example ambient temperature plus the heat of compression), liquefaction also takes place of the portion of the overhead product which is withdrawn from the head of the distillation column and is used for providing the ethylene product in supercritical state, in this case a very large temperature difference has to be overcome and thus a large amount of heat has to be extracted. This is discussed again with reference to the enthalpy/pressure diagram in FIG. 5. After the pressurisation in the liquid state, a considerable amount of energy then has to be supplied again in order to effect heating to ambient conditions for providing the ethylene product.

By contrast, in order to provide the ethylene product in a supercritical state, the present invention makes it possible, as discussed in greater detail with reference to the enthalpy/pressure diagram in FIG. 6 as well, to dispense with correspondingly large temperature jumps. Merely the first portion of the overhead product withdrawn from the head of the distillation column, which product is used as reflux, has to be subjected to correspondingly intensive cooling and liquefaction. The second portion is compressed in multiple stages, in each case merely the heat of compression being extracted at a temperature level above ambient conditions. In this case, merely cooling to for example approximately 40° C. in each case is necessary, which can be brought about using cooling water. By dispensing with intermediate liquefaction, the present invention makes it possible to save on correspondingly cost-intensive, cold-resistant materials.

Generally in the prior art the preconception exists that provision of a pressurised product in a supercritical state is particularly advantageous if, as discussed with reference to the prior art, intermediate liquefaction and pressurisation of the liquefaction product in the liquid state is carried out here. In the context of the present invention it has however been found that the energy-related advantages of compression in stages in the gaseous state distinctly outweigh any disadvantages.

In the context of the invention, as mentioned, a multi-stage compression from the distillation pressure level via a plurality of intermediate pressure levels to a supercritical pressure level is carried out for converting the second portion into the supercritical state. In this case, the second portion is converted predominantly or exclusively directly from the gaseous into the supercritical state in the multi-stage compression.

The intermediate pressure levels mentioned comprise in this case at least a first intermediate pressure level, which is from 18 to 25 bar, in particular 22 to 23 bar, for example approximately 22.5 bar. Compression to such an intermediate pressure level is particularly advantageous because at this intermediate pressure level the first portion which in this respect is likewise subjected to the multi-stage compression and which is used as reflux to the distillation column, can be discharged. Compression of the first portion prior to liquefaction is expedient in order to be able to bring about the liquefaction at sufficiently high temperatures or using the refrigerants available.

As is also discussed below, such a first portion, after corresponding compression, in addition to the cooling in further heat exchangers, can be used as a heat transfer medium in a bottom evaporator of the distillation column. In this manner, a heat pump effect having particularly advantageous energy efficiency is achieved. In other words, the first portion is therefore advantageously compressed in the multi-stage compression from the distillation pressure level to the first intermediate pressure level, is then liquefied and used as the reflux. Furthermore, as mentioned, it is advantageous if the distillation column is operated using a bottom evaporator which is heated using the first portion which is compressed to the first intermediate pressure level.

Advantageously, the multi-stage compression in the context of the present invention also comprises the compression of refrigerant from a refrigerant circuit which comprises at least three partial circuits which are operated at different pressure levels. Ethylene refrigerant is used in corresponding processes and installations at different points, for example in a demethanizer or in other separation steps. Methods and installations for processing gas mixtures which are produced by steam cracking typically comprise partial circuits at different pressure and thus temperature levels which are operated using ethylene refrigerant. Typically in this case a low-pressure refrigerant circuit is provided which is operated slightly above or slightly below the atmospheric pressure level, typically at from 0.5 to 1.5 bar, in particular from 1.0 to 1.1 bar, for example approximately 1.05 bar (referred to below as "first starting pressure level"). Refrigerant in such a low-pressure refrigerant circuit has for example a temperature level of from approximately −95 to −100° C. A medium-pressure refrigerant circuit is typically operated at a pressure level of from approximately 2.5 to 3.5 bar, in particular from 2.8 to 3.2 bar, for example approximately 3 bar (referred to below as "second starting pressure level"). Its refrigerant has a temperature level of typically from approximately −75 to −85° C. Finally, what is known as a high-pressure refrigerant circuit is present which is operated at a pressure level of typically from approximately 5 to 10 bar, in particular from 8 to 9 bar, for example approximately 8.1 bar, i.e. the distillation pressure level. The refrigerant of the high-pressure refrigerant circuit has a temperature level of typically from −55 to −65° C., in particular approximately −57° C.

Advantageously, in the multi-stage compression which is used in the context of the invention, furthermore a refrigerant containing predominantly or exclusively ethylene is therefore compressed from a plurality of starting pressure levels which lie below the distillation pressure level, and from the distillation pressure level to the first intermediate pressure level. In this manner, the multi-stage compressor used according to the invention or the corresponding compression can also be used for providing refrigerant or for charging the aforementioned partial circuits with refrigerant. In this manner, an open refrigerant circuit is produced which can be operated in a particularly flexible and energy-saving manner.

In the context of the present invention, it is expedient if the multi-stage compression comprises compression to a further, i.e. second, intermediate pressure level, which is from 35 to 45, in particular from 38 to 42 bar, for example approximately 40.2 bar. This is particularly advantageous because, in this case, a first compressor stage can be provided for compressing from the first to the second starting pressure level, a second compressor stage can be provided for compressing from the second starting pressure level to the distillation pressure level, a third compressor stage can be provided for compressing from the distillation pressure level to the first intermediate pressure level, and a fourth compressor stage can be provided for compressing from the first intermediate pressure level to the second intermediate pressure level, which stages can be driven at the same speed in particular by means of a first common shaft. Therefore a common prime mover can be provided for driving these compressor stages, because the compressor load is distributed substantially uniformly among the aforementioned compressor stages.

Advantageously, after the compression to the second intermediate pressure level in the context of the present invention, furthermore compression to a third intermediate pressure level, which is from 60 to 80 bar, in particular 65 to 75 bar, for example approximately 70.4 bar, takes place, from which the second portion is then compressed to the supercritical pressure level of from 100 to 150 bar, in particular from 120 to 130 bar, for example approximately 125.6 bar.

Advantageously, a fifth compressor stage is used for compressing from the second to the third intermediate pressure level, and a sixth compressor stage is used for compressing from the third intermediate pressure level to the supercritical pressure level. Advantageously, the fifth and sixth compressor stages may be driven at the same speed by means of a second common shaft. In this manner, particularly good adaptability to the respective compression requirements is ensured and advantages in terms of control are obtained by the separate, but in each case grouped, driving of both the first to fourth compressor stages and of the fifth and sixth compressor stages. In particular, provision may be made in this case for the first and the second common shaft to be coupled together by means of a gear mechanism. In this manner, both the first to fourth compressor stages and the fifth and sixth compressor stages can be operated at different speeds.

Downstream of the aforementioned compressor stages, aftercooling by means of suitable aftercoolers, which are usually operated using cooling water, typically takes place. In this case, a corresponding aftercooler is not necessarily provided downstream of the first compressor stage. Downstream of the second compressor stage, although there is a corresponding aftercooler, due to the simultaneous supply of ethylene refrigerant at the corresponding pressure level the third compressor stage is, however, supplied with fluid at a temperature of typically approximately 18° C. The fluid is supplied to the fourth, fifth and sixth compressor stages in each case at typically approximately 40° C., which it reaches owing to the aftercoolers which are operated using water. Portions of the fluids compressed in each case in the compressor stages can also be returned (what are known as "kickbacks"), in particular in order to ensure better ability to regulate the compression.

Advantageously, the method according to the invention is used in the context of a steam cracking process, i.e. the gas mixture containing predominantly or exclusively ethylene and ethane is formed using a cracked gas from a steam cracking process. As mentioned, various methods are known from the prior art for forming a corresponding gas mixture.

The present invention also relates to an installation for obtaining an ethylene product in a supercritical state, comprising a distillation column which is set up to separate a gas mixture containing predominantly or exclusively ethylene and ethane at a distillation pressure level of from 5 to 15 bar into an overhead product containing predominantly or exclusively ethylene and a bottom product containing predominantly or exclusively ethane, means being provided which are set up to withdraw the overhead product in the gaseous state from the head of the distillation column and to liquefy a first portion and return it as reflux to the distillation column, and to convert a second portion into a supercritical state and use it as the ethylene product. According to the invention, a multi-stage compressor is provided which is set up for converting the second portion into the supercritical state by compressing from the distillation pressure level via a plurality of intermediate pressure levels to a supercritical pressure level, the second portion in the multi-stage compressor being converted predominantly or exclusively from the gaseous into the supercritical state.

A corresponding installation is advantageously set up for carrying out a method as has been discussed previously in detail, and has corresponding means for this purpose. Reference is therefore expressly made to the features and advantages discussed with respect to the method.

The invention will now be discussed in greater detail below with reference to the accompanying drawings, which show aspects of the present invention in comparison with aspects not in accordance with the invention.

BRIEF DESCRIPTION OF THE DRAWINGS

In the figures, corresponding elements are indicated using identical reference signs and for the sake of clarity will not be discussed more than once.

FIG. 1 shows a method not in accordance with the invention for obtaining an ethylene product in the form of a schematic process flow diagram.

Figure 1:
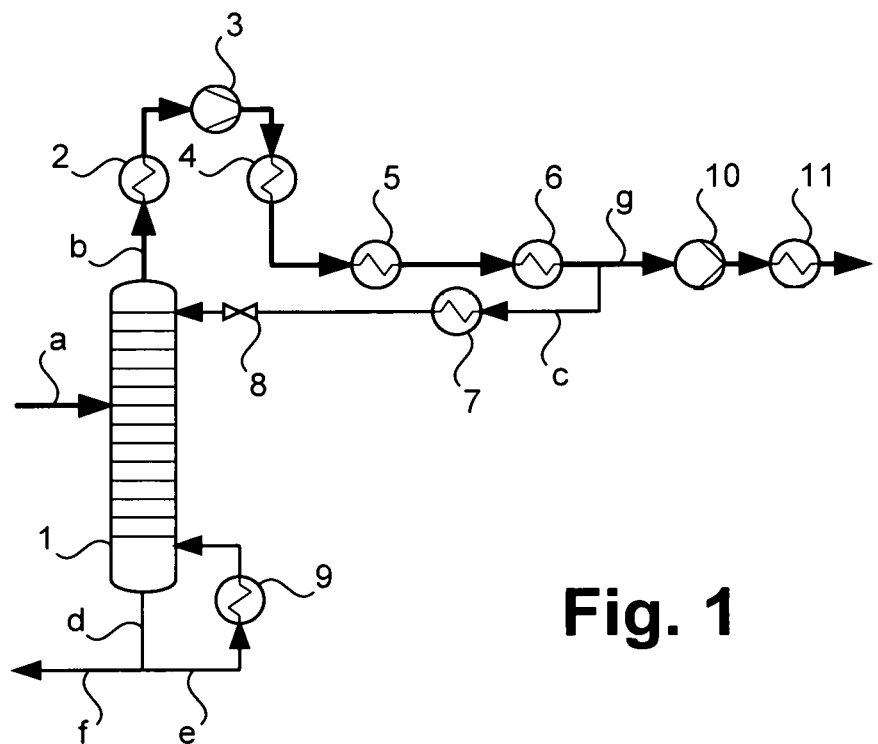
FIG. 1 shows a method not in accordance with the invention in the form of a schematic process flow diagram.

The method comprises the use of a distillation column 1 which is operated at a pressure level of from 5 to 15 bar, in particular from 8 to 10 bar, for example approximately 8.1 bar, i.e. the distillation pressure level which has been mentioned several times. It is therefore a low-pressure C2 splitter as discussed at the beginning.

The distillation column 1 is supplied with a gas mixture containing predominantly or exclusively ethylene and ethane, in the form of a stream a at a suitable height. In the distillation column 1, the gas mixture which is supplied in the form of the stream a is separated into an overhead product containing predominantly or exclusively ethylene and a bottom product containing predominantly or exclusively ethane.

The overhead product in this case is withdrawn in gaseous state from the head of the distillation column 1 in the form of a stream b, heated in a heat exchanger 2 to for example ambient temperature, and compressed in a compressor 3 to a pressure level of more than 20 bar, for example 22.5 bar. After compression in the compressor 3, the gas mixture of stream b is cooled and liquefied in heat exchangers 4 to 6. After the cooling in the heat exchanger 6, some of the fluid of stream b is supplied in the form of a stream c for further cooling in a heat exchanger 7. Then pressure relief of the fluid of stream c to the pressure level of distillation column 1 takes place in a valve 8. The fluid of stream c is charged as reflux at the head of the distillation column 1.

From the bottom of the distillation column 1, the bottom product accumulated there is withdrawn in the form of a stream d. Some of the bottom product is passed in the form of a stream e through a bottom evaporator 9, is boiled there, and returned into the distillation column 1, where it ascends in gaseous form. In particular, the heat exchanger 6 and the heat exchanger 9 may also be thermally coupled or be in the form of a common heat exchanger. In this manner, as previously discussed, a heat pump effect is obtained. A further portion of the bottom product of the stream d is carried out in the form of stream f. Since the stream f contains predominantly or exclusively ethane, it may be supplied for example into an upstream steam cracking apparatus.

The stream g, which comprises the overhead product of stream b that is not returned to the distillation column 1 in the form of the stream c, and thus comprises predominantly or exclusively ethylene, is pressurised in liquid state by means of a pump 10 in the method not in accordance with the invention. The pressure increase therefore takes place up to a supercritical pressure level. Starting from the liquid state, the stream g is heated in a further heat exchanger 11 in order to provide the ethylene product in the supercritical state.

Figure 2:
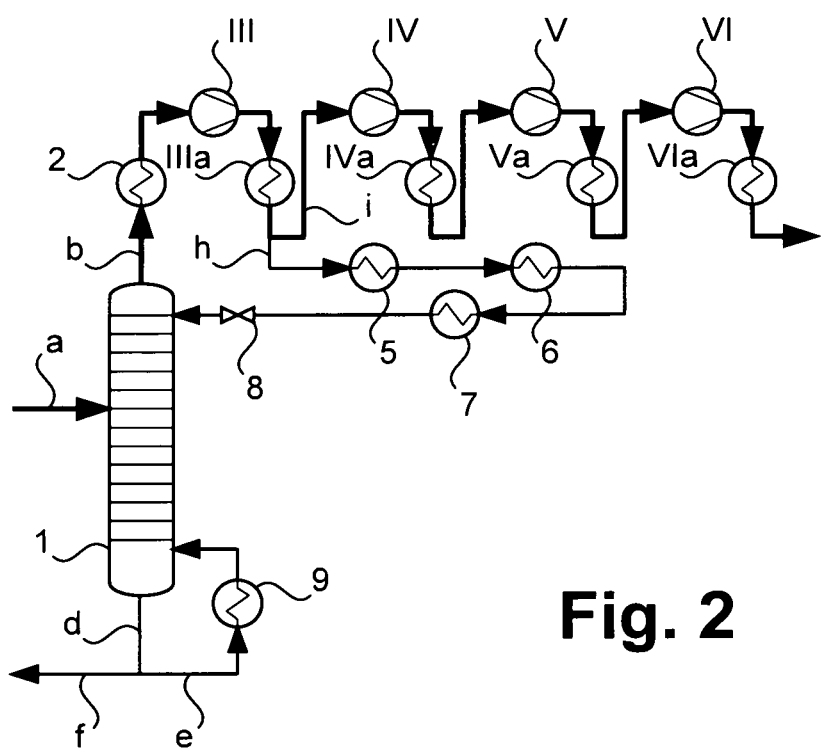
FIG. 2 shows a method according to one embodiment of the invention in the form of a schematic process flow diagram.

FIG. 2 shows a method for obtaining an ethylene product in a supercritical state according to a particularly preferred embodiment of the invention, likewise in the form of a schematic process flow diagram. Elements which in this case correspond to those of the method not in accordance with the invention of FIG. 1 are indicated by identical reference signs and, as mentioned, for the sake of clarity will not be discussed more than once.

Also in the context of the method according to one embodiment of the invention shown in FIG. 2, the stream b is superheated in a heat exchanger 2. After the heating, the stream b is then, however, compressed in compressor stages of a multi-stage compressor, which here are denoted by III to VI for the sake of better comparability with FIG. 4. Downstream of the compression, aftercooling in aftercoolers denoted by IIIa to VIa takes place in each case. Downstream of the compression in compressor stage III, a stream h which in principle corresponds to the stream c of FIG. 1 is branched off and is used as reflux to the distillation column 1. This stream h is cooled and liquefied in the heat exchangers 5, 6 and 7, it being possible here, too, for the heat exchanger 6 to be thermally coupled to the heat exchanger 9 or to be in the form of a common heat exchanger. After corresponding cooling and liquefaction, the stream h is fed back to the distillation column via the valve 8 and is used there as reflux.

In the compressor stages III to VI, remainder which is not branched off in the form of the stream h, here denoted by i, is compressed to a supercritical pressure level, no intermediate liquefaction taking place. The compressor stage III in this case compresses the stream h from the distillation pressure level discussed above to the first intermediate pressure level, the compressor stage IV compresses the stream h from the first intermediate pressure level to the second intermediate pressure level, the compressor stage V compresses the stream h from the second intermediate pressure level to the third intermediate pressure level, and the compressor stage VI compresses the stream h from the third intermediate pressure level to the supercritical pressure level. The pressure levels have been previously discussed.

Figure 3:
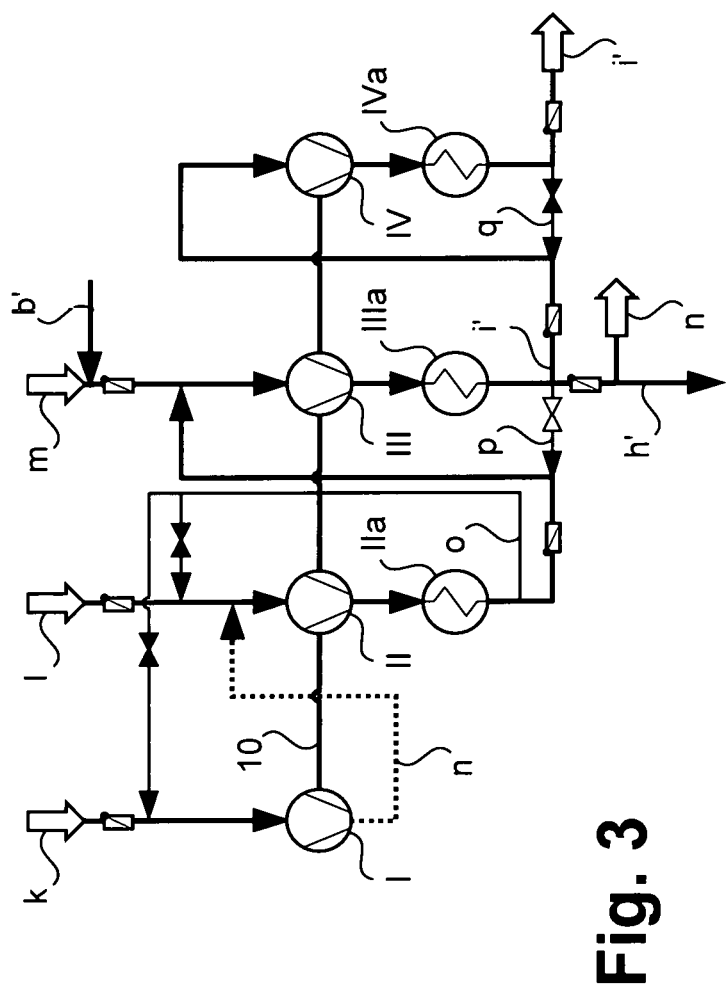
FIG. 3 shows a compression not in accordance with the invention in the form of a schematic process flow diagram.

In FIG. 3, a compression in accordance with an embodiment not in accordance with the invention is shown schematically in the form of a process flow diagram. Here, compressor stages of a multi-stage compressor are shown by I to IV, the compressor stages III and IV of the compression shown in FIG. 3 corresponding substantially to the compressor stages III and IV of the compression shown in FIG. 2, but here the compressor stages V and VI are missing. These are shown in the following FIG. 4, which shows a compression according to one embodiment of the invention. The compression shown in FIG. 3 may in such cases be used in conjunction with a low-pressure C2 splitter, in which no compression to a supercritical pressure level and thus no provision of an ethylene product in supercritical state is called for. In a corresponding compression, depending on the required pressure level, it is also possible to dispense with the fourth compression stage IV. In this case, the ethylene product is discharged at the pressure-side pressure level of the third compression stage III.

The compression shown in FIG. 3 is in addition integrated in an ethylene refrigerant circuit comprising three partial circuits, refrigerant streams being denoted by k, l and m. As mentioned, an ethylene product in the supercritical state is not provided in the compression according to FIG. 3. Here too, however, an overhead product can be fed in from the head of a distillation column 1 as shown in FIG. 2. For the sake of better differentiation, a corresponding stream is denoted here by b'. The stream k represents low-pressure refrigerant, which is provided at the first starting pressure level and a temperature level of from approximately −95 to −100° C. The stream l denotes medium-pressure refrigerant, which is provided at the second starting pressure level and a temperature level of from approximately −75 to −85° C. The stream m denotes high-pressure refrigerant, which is provided at the distillation pressure level and a temperature level of from approximately −55 to −65° C. The corresponding streams, as shown in FIG. 3, are supplied to the compressor stages I to III optionally after superheating. The transferring of the refrigerant from the compressor stage I to the compressor stage II takes place directly in the machine without intermediate cooling, and is shown here in the form of a stream n represented by a dotted line.

The compressor stages I to IV may be interconnected by a common shaft, here denoted by 10. The fluid compressed in the compressor stage II is cooled in the heat exchanger IIa and at least a predominant portion is then supplied to the compressor stage III. A certain portion can also be returned to the compressor stage I in the form of what is known as a kickback. Correspondingly, the fluid is compressed in the compressor stage III and then cooled in the heat exchanger IIIa. However, some can be returned before the compressor stage III, as shown by the stream p. A further portion, as shown here in the form of the stream h', may be used as reflux to the distillation column. A further stream, as shown here by n, is returned into the refrigerant circuit at the first intermediate pressure level, to which the compressor stage III compresses the fluid. As is not shown here, the refrigerant of the stream n can then undergo pressure relief to the previously discussed pressure levels of the partial circuits or streams k, l and m. The remaining portion, as shown here in the form of the stream i', is supplied to the fourth compressor stage IV, is compressed there to the second intermediate pressure level and then cooled in an aftercooler IVa. However, a portion, as shown here in the form of the stream q, can be returned before the compressor stage IV. The remainder, as shown here in the form of the stream i', can be provided as ethylene product at a subcritical pressure level.

Figure 4:
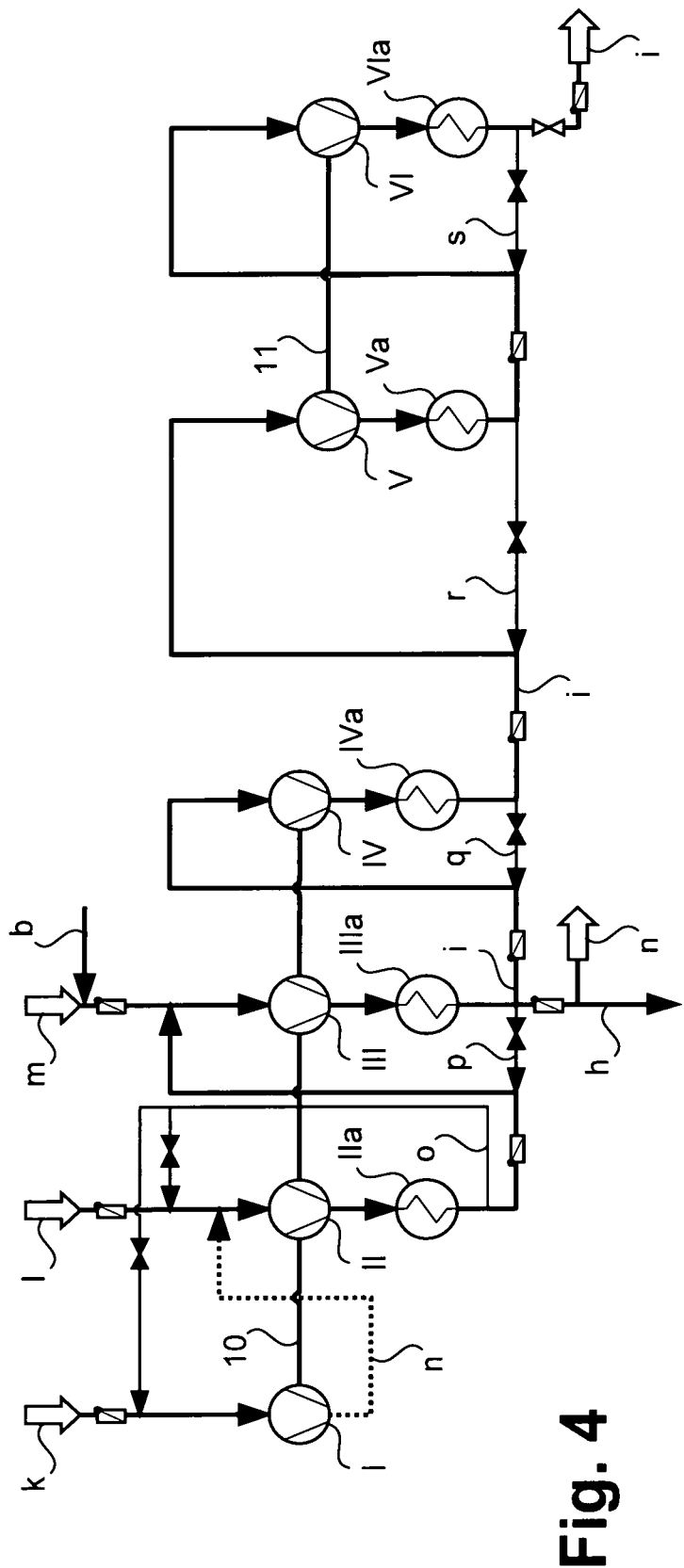
FIG. 4 shows a compression according to one embodiment of the invention in the form of a schematic process flow diagram.

By contrast, the compression, shown in FIG. 4, according to one embodiment of the invention comprises the two further compressor stages V and VI, which are already shown in FIG. 2. These are in principle operated comparably to the compressor stage IV, but compress the fluid of the stream, which here corresponds to the stream i of FIG. 2 and therefore is denoted identically here, further to pressure levels which are higher once again. The compressor stage V in this case compresses the fluid to the third intermediate pressure level; in the aftercooler Va the fluid in this case is cooled to a temperature of for example approximately 40° C. The compressor stage VI finally compresses the fluid to the supercritical pressure level (the third intermediate pressure level may also already be supercritical), cooling to a temperature level of for example approximately 40° C. taking place here too in the aftercooler VIa.

The advantages of the present invention over the method not in accordance with the invention will be discussed below with reference to the enthalpy/pressure diagrams shown in FIGS. 5 and 6. In these, in each case a pressure in MPa is plotted on the ordinate against an enthalpy in kJ/kg on the abscissa. 101 (bold, continuous line) shows in each case the two-phase line of the enthalpy/pressure diagrams. The isotherm lines are (in part) denoted by their respective temperatures.

Figure 5:
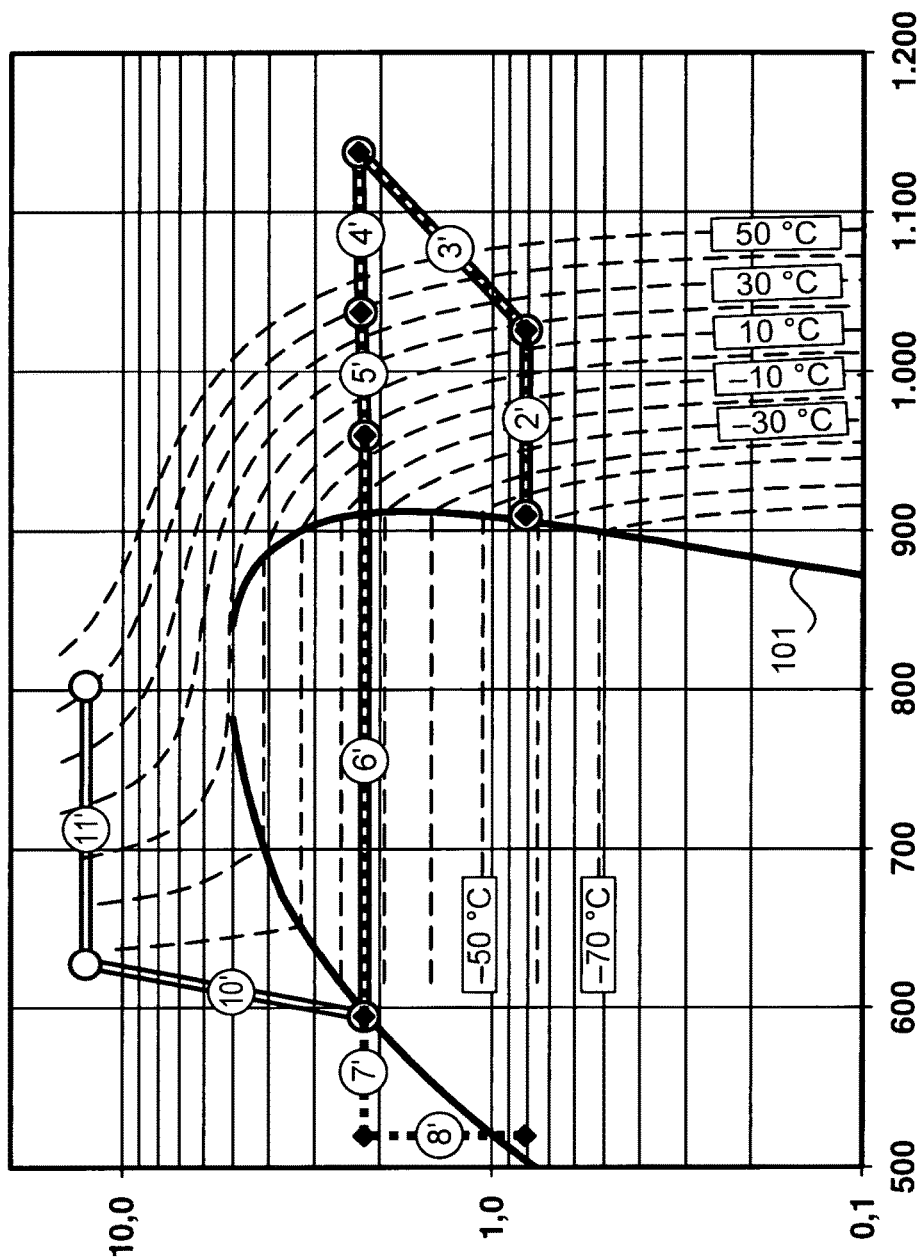
FIG. 5 is an enthalpy/pressure diagram of the method not in accordance with the invention which is shown in FIG. 1.

As mentioned, FIG. 5 is the enthalpy/pressure diagram of the method not in accordance with the invention shown in FIG. 1. For greater clarity, in this case the changes in state brought about by the apparatus shown in FIG. 1 are shown in the enthalpy/pressure diagram by the corresponding reference signs, which in each case are provided with a prime for delimitation purposes. The treatment of the ethylene product (stream g in FIG. 1) is shown in the form of a double line, and the treatment of the reflux to the distillation column (stream c in FIG. 1) in the form of a bold dotted line. Where these streams have a common path (stream b in FIG. 1), the double line and the dotted line are shown superimposed.

Due to the heating in the heat exchanger 2 according to FIG. 1, here denoted by 2', the fluid of the stream b withdrawn from the head of the distillation column absorbs energy. Then, as shown here by 3', compression takes place in the compressor 3. To this end, the fluid undergoes both a pressure increase and heating due to the absorption of heat of compression. Then the fluid of the stream b is cooled in the heat exchangers 4 to 6 and in so doing is liquefied. This is shown in the enthalpy/pressure diagram of FIG. 5 by 4' to 6'. As denoted in the enthalpy/pressure diagram by 7' and 8', the fluid of the stream c is then subjected to further cooling in the heat exchanger 7 and then undergoes pressure relief in the valve 8. As a result, the fluid passes into the two-phase region and is accordingly fed into the distillation column 1 in two-phase form. By contrast, the stream g, which is not returned to the distillation column, is pressurised in liquid form in the pump 10, as denoted in the enthalpy/pressure diagram of FIG. 5 by 10', and as a result undergoes a corresponding pressure and temperature increase, compression to the previously discussed supercritical values being carried out. Heating of the supercritical fluid in the heat exchanger 11 follows.

As can be seen from the enthalpy/pressure diagram in FIG. 5, here, due to the cooling in the heat exchangers 4 to 6, a distinct temperature difference has to be overcome, therefore a considerable amount of energy is extracted from the fluid of the stream b. Then, a considerable amount of energy is supplied again for heating the fluid of the stream g in the heat exchanger 11. This, as has been established according to the invention, does not prove to be advantageous in terms of energy.

Figure 6:
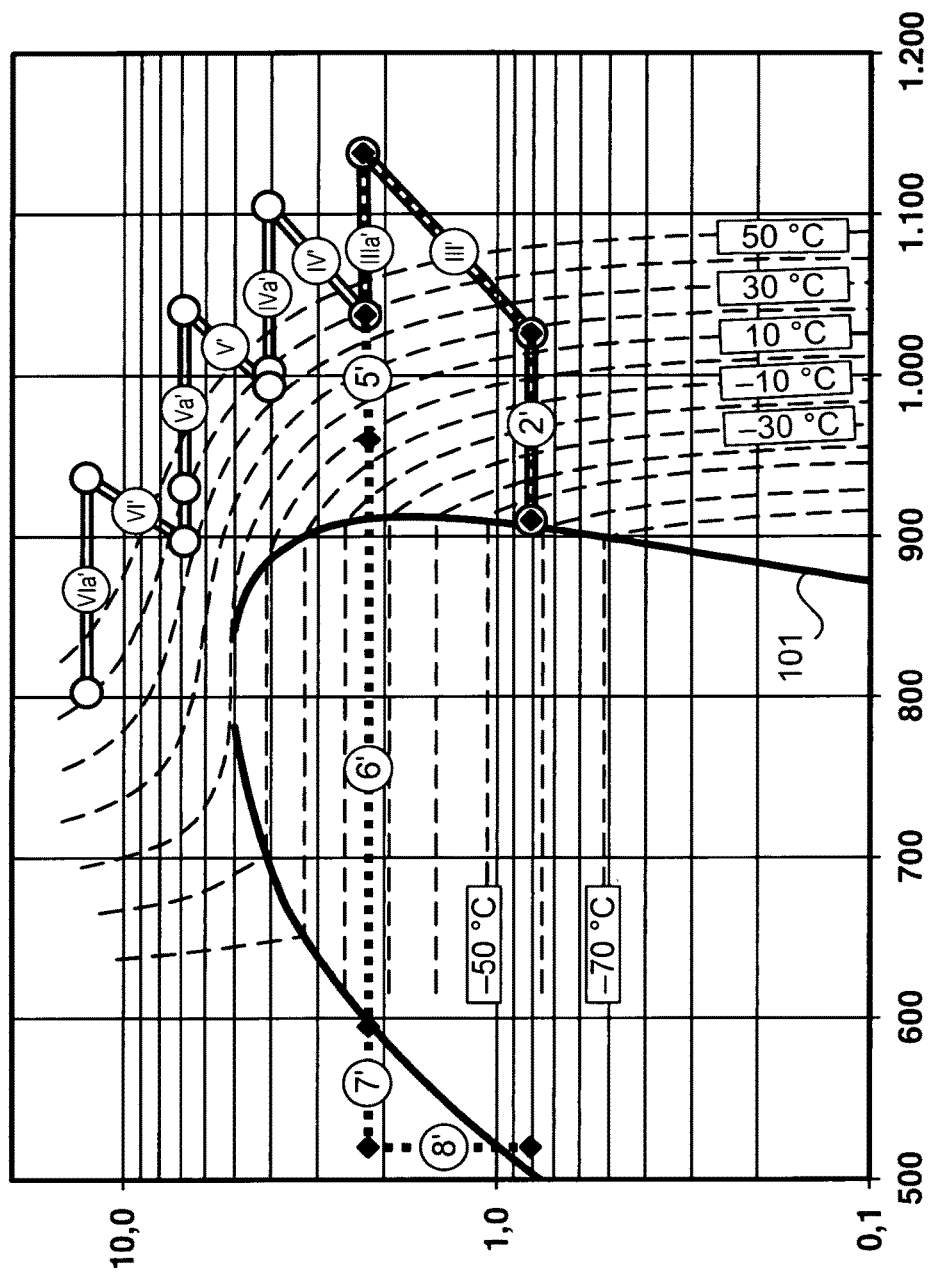
FIG. 6 is an enthalpy/pressure diagram of the method shown in FIG. 2 according to one embodiment of the invention.

As mentioned, FIG. 6 is the enthalpy/pressure diagram of the method in accordance with the embodiment shown in FIG. 2. Here too, the changes in state which correspond to the apparatus shown in FIG. 2 are indicated by reference signs having primes. The treatment of the ethylene product (stream i in FIG. 2) is in the form of a double line, and the treatment of the reflux to the distillation column (stream h in FIG. 2) is shown in the form of a bold dotted line. Where these streams have a common path (stream b in FIG. 2), here too the double line and the dotted line are shown superimposed.

The heating in the heat exchanger 2, denoted by 2' in the enthalpy/pressure diagram 6, corresponds in this case first of all to the heating in the method not in accordance with the invention according to FIG. 2. The same also applies to the compression in compression stage III, denoted by III' in FIG. 5. After this compression, cooling takes place as designated by IIIa' in FIG. 6. This takes place for example to a temperature level of approximately 40° C., as can be seen here from the corresponding isotherms. As denoted by the in FIG. 6 by a broken line, now only some of the fluid of stream b, namely the fluid of stream h, is liquefied, however. Here, the heat exchangers 5 to 7 are used; the corresponding cooling operations are shown by 5' to 7' in the enthalpy/pressure diagram of FIG. 6. The equivalent also applies to the pressure relief in the relief valve 8 shown by 8'.

The remainder in the form of the stream i is now compressed in the compressor stage IV, shown in FIG. 6 by IV', then cooled in the aftercooler VIa, shown in FIG. 6 by VIa', etc. The further compression and cooling stages can be seen directly from FIG. 6. After the compression in the compressor stage VI and the cooling in the aftercooler VIa, the ethylene product is present at a supercritical pressure level of typically approximately 125.6 bar and at a temperature level of for example approximately 40 bar.

The invention claimed is:

1. A method for obtaining an ethylene product in a supercritical state, in which a gas mixture containing predominantly or exclusively ethylene and ethane is separated in a distillation column, which is operated at a distillation pressure level of from 5 to 15 bar, into an overhead product containing predominantly or exclusively ethylene and a bottom product containing predominantly or exclusively ethane, the overhead product being withdrawn in the gaseous state from the head of the distillation column and a first portion thereof being liquefied and returned as reflux to the distillation column and a second portion thereof being converted into a supercritical state and being used as the ethylene product, characterised in that, for converting the second portion into the supercritical state, multi-stage compression from the distillation pressure level via a plurality of intermediate pressure levels to a supercritical pressure level is carried out, the second portion in the multi-stage compression being converted predominantly or exclusively directly from the gaseous into the supercritical state.

2. The method according to claim 1, in which the intermediate pressure levels comprise a first intermediate pressure level which is from 18 to 25 bar.

3. The method according to claim 2, in which the first portion is compressed in the multi-stage compression from the distillation pressure level to the first intermediate pressure level, is then liquefied and used as the reflux.

4. The method according to claim 3, in which the distillation column is operated by a bottom evaporator which is heated using the first portion which is compressed to the first intermediate pressure level.

5. The method according to claim 2, in which furthermore a refrigerant containing predominantly or exclusively ethylene is compressed in the multi-stage compression from a plurality of starting pressure levels which lie below the distillation pressure level, and also from the distillation pressure level to the first intermediate pressure level.

6. The method according to claim 5, in which the starting pressure levels comprise a first starting pressure level, which is from 0.5 to 1.5 bar, and a second starting pressure level, which is from 2 to 4 bar.

7. The method according to claim 6, in which the intermediate pressure levels further comprise a second intermediate pressure level, which is from 35 to 45 bar.

8. The method according to claim 7, in which a first (I) compressor stage is used for compressing from the first to the second starting pressure level, a second (II) compressor stage is used for compressing from the second starting pressure level to the distillation pressure level, a third (III) compressor stage is used for compressing from the distillation pressure level to the first intermediate pressure level, and a fourth (IV) compressor stage is used for compressing from the first intermediate pressure level to the second intermediate pressure level, the first to fourth compressor stages (I-IV) being driven at the same speed by means of a first common shaft.

9. The method according to claim 8, in which the intermediate pressure levels further comprise a third intermediate pressure level, which is from 60 to 80 bar, and in which the supercritical pressure level is from 100 to 150 bar.

10. The method according to claim 9, in which, a fifth (V) compressor stage is used for compressing from the second to the third intermediate pressure level, and a sixth (VI) compressor stage is used for compressing from the third intermediate pressure level to the supercritical pressure level, the fifth and the sixth compressor stages (V, VI) being driven at the same speed by means of a second common shaft.

11. The method according to claim 10, in which the first and the second common shaft are coupled together by means of a gear mechanism.

12. The method according to claim 1, in which the gas mixture containing predominantly or exclusively ethylene and ethane is formed using a cracked gas from a steam cracking process.

* * * * *